(12) United States Patent
Rosenberg et al.

(10) Patent No.: US 7,857,775 B2
(45) Date of Patent: Dec. 28, 2010

(54) METHOD FOR SOFT TISSUE TREATMENT

(75) Inventors: Avner Rosenberg, Beit Shearim (IL); Michael Kreindel, Zichron Ya'acov (IL)

(73) Assignee: Syneron Medical Ltd., Yokeneam Illit (IL)

( * ) Notice: Subject to any disclaimer, the term of this patent is extended or adjusted under 35 U.S.C. 154(b) by 1038 days.

(21) Appl. No.: 11/079,887

(22) Filed: Mar. 15, 2005

(65) Prior Publication Data

US 2006/0211958 A1    Sep. 21, 2006

(51) Int. Cl.
*A61H 7/00* (2006.01)
*A61H 23/00* (2006.01)

(52) U.S. Cl. ............................. 601/7; 601/9; 601/148; 601/15

(58) Field of Classification Search ............... 601/2–4, 601/45, 48, 70, 72, 148, 6–12, 15
See application file for complete search history.

(56) References Cited

U.S. PATENT DOCUMENTS

| | | | | |
|---|---|---|---|---|
| 3,094,983 A | * | 6/1963 | MacLeod | ...................... 601/9 |
| 3,465,748 A | * | 9/1969 | Kravchenko | .................... 601/6 |
| 4,428,368 A | * | 1/1984 | Torii | .............................. 601/9 |
| 4,697,579 A | * | 10/1987 | Wessels et al. | ................. 601/4 |
| 5,143,063 A | | 9/1992 | Fellner | |
| 5,219,401 A | * | 6/1993 | Cathignol et al. | ........... 600/439 |
| 5,540,702 A | | 7/1996 | Walz et al. | |
| 5,725,482 A | | 3/1998 | Bishop | |
| 5,897,495 A | * | 4/1999 | Aida et al. | .................. 600/411 |
| 6,298,264 B1 | | 10/2001 | Zhong et al. | |
| 6,607,498 B2 | | 8/2003 | Eshel | |
| 6,736,784 B1 | | 5/2004 | Menne et al. | |
| 2003/0135135 A1 | * | 7/2003 | Miwa et al. | .................... 601/2 |
| 2004/0039312 A1 | | 2/2004 | Hillstead et al. | |
| 2004/0215110 A1 | | 10/2004 | Kreindel | |
| 2005/0027218 A1 | * | 2/2005 | Filtvedt et al. | .............. 601/152 |
| 2009/0036803 A1 | * | 2/2009 | Warlick et al. | ................. 601/4 |

* cited by examiner

*Primary Examiner*—Danton DeMille
(74) *Attorney, Agent, or Firm*—Browdy and Neimark, PLLC

(57) ABSTRACT

A method and system for non-invasive treatment of a soft tissue, such as adipose tissue, muscle tissue or connective tissue. The apparatus comprises an applicator configured to apply a pressure pulse to the skin surface having a negative pressure phase with respect to ambient pressure. The method comprises applying at least one pressure pulse to the skin surface overlying the soft tissue, where the pressure pulse has at least one negative pressure phase.

8 Claims, 4 Drawing Sheets

METHOD FOR SOFT TISSUE TREATMENT

FIELD OF THE INVENTION

This invention relates to medical devices and more specifically to such devices and methods for non-invasive treatment of soft tissues such as adipose tissue.

BACKGROUND OF THE INVENTION

Adipose tissue is located under the skin layer. Thus, energy applied to the skin surface to degrade adipose tissue must pass through the skin layer to reach the adipose tissue without damaging the skin.

Various devices have been used for the treatment of adipose tissue. One popular method of fat treatment is liposuction. This is an invasive technique involving mechanical disruption of the tissue fat with subsequent suction of the resulting debris out of the body. The main disadvantage of this method is its invasive character.

U.S. Pat. No. 5,143,063 describes a method for treating adipose tissue based on thermal destruction of fat by exposing adipose tissue to focused microwave or ultrasound waves. The intensity and the focusing of the energy is determined so as to selectively destroy fat cells without damaging the skin or deep tissues.

U.S. patent application Ser. No. 2004/0039312 filed February 2003 discloses the application of high intensity focused ultrasound (HIFU) for destruction of adipose tissue. U.S. Pat. No. 6,607,498 discloses HIFU pulsed so as to produce cavitation, which selectively destroys fat cells.

U.S. Pat. No. 5,725,482 discloses superposition of ultrasound waves from two or more sources to create a wave having high intensity localized at the adipose tissue to be treated.

High intensity focused ultrasound (HIFU), whether the mechanism is cavitation, thermal treatment or another form of treatment, has a basic disadvantage, due to the small focal diameter, which is typically only a few millimeters. This focusing is necessary for preventing damage to the skin layer. However, it makes it very difficult to treat large areas of soft tissue, as the applicator head has to be moved over the skin surface in very small steps. Because of the pliable character of the adipose tissue, movement of the applicator over the skin surface displaces the adipose tissue to another position, thereby creating a risk of over treating some tissue volumes and under treating other tissue volumes.

SUMMARY OF THE INVENTION

The present invention provides a method and apparatus for the treatment of soft tissue, such as adipose tissue, muscle tissue or connective tissue. In accordance with the invention, a pressure pulse is applied to a region of skin overlying a volume of soft tissue. The pressure pulse has at least one negative pressure phase with respect to the ambient pressure. The negative pressure pulls the tissue to be treated outwards from the body. In a preferred embodiment, the negative pressure phase is followed by a positive pressure phase in order to return the tissue back to its original position. In this way, a train of pulses, each pulse having a negative pressure phase and a positive pressure phase an be applied to the skin surface.

In the case of adipose tissue, the action of the negative phases causes destruction of fat cells, with little or no damage to other tissues, since fat cells are larger and weaker than most other cells. The intensity and time profiles of the pressure pulse are selected to cause maximal destruction of the adipocytes, with minimal damage to other tissues. In the case of other types of soft tissues, such as muscle tissue or connective tissue, the pulses create a massaging effect of the tissue.

In one embodiment of the invention, pressure pulses are generated using electrical evaporation of a liquid such as water, preferably a saline solution. A spark is generated in the liquid that generates an oscillating vapor bubble in the liquid which creates an oscillating pressure pulse having positive and negative phases with respect to the ambient pressure.

According to another embodiment of the invention, pressure pulses on the skin surface are generated by a plate applied to the skin surface that is made to oscillate by magnetic forces. The magnetic forces may be produced, for example, using solenoid actuators, driven by a current pulse. The current pulse generates magnetic fields which alternately pull and push a rod attached to the plate. The rod is adhered to the skin surface via a coupling agent that may be a volume of liquid, a flexible element or a solid element covered with gel. The plunger may first push upon the skin surface (positive pressure phase) and then pull on the skin surface (negative pressure phase). This push-pull action thus generates a pressure pulse in the body tissue to be treated having a positive phase and a negative phase.

The magnetic force may also be generated by driving a high current in a coil. In proximity to this coil a conducting metal sheet is positioned. Eddy currents in the metal sheet produce a force that pushes the metal sheet away from the coil. Another embodiment may use two adjacent coils driven with a current pulse. According to the relative polarity of the current in the two coils, a force of attraction or repulsion between the coils is generated.

Another embodiment of the invention is based on a compressed gas actuator, or a vacuum actuator. These actuators generate a push-pull action by controlled application and removal of pressure pulses of a gas such as air into a piston.

The negative pressure part may be between 0.1 Bar below ambient to 10 Bars below ambient and more preferably between 0.1 Bar to 3 Bar below ambient pressure. The intensity of the positive pressure phase, when present, may be, for example, between 1 to about 30 Bars above ambient pressure, and more preferably between 2 to 10 bars above ambient. The pressure pulse may have, for example, a negative part of between 0.1 millisecond and 100 millisecond duration, more preferably between 1 to 10 milliseconds and a positive part of between 0.01 to 1 millisecond duration. In another preferred embodiment, the negative part is between 1 to 10 milliseconds, while the positive part is much longer than the negative part and may be, for example, 10-100 msec. A train of pulsewaves having a frequency of 10-100 Hz may thus be applied to the skin surface. In the case of the treatment of adipose tissue, the temperature of the adipose tissue may be raised during the treatment in order to enhance the effect of the cell disruption by the pressure pulse. The adipose tissue is preferably heated to a temperature higher than normal body tissue temperature (37° C.), but not high enough to damage the skin surface, prior to and/or simultaneously with the application of the pressure pulse. Any known method for heating adipose tissue may be used, such as an RF current through the tissue via conducting electrodes applied to the surface of the skin, radiation of the skin surface with light from a flash lamp or laser, microwave power radiated into the tissue, and high intensity ultrasound. The heat is preferably focused on the tissue volume to be destroyed, and is preferably applied at a depth below the skin surface greater than about 5 mm where the adipose tissue is located. To further reduce unwanted damage to skin layers, in a preferred embodiment, cooling means are applied to the skin surface.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
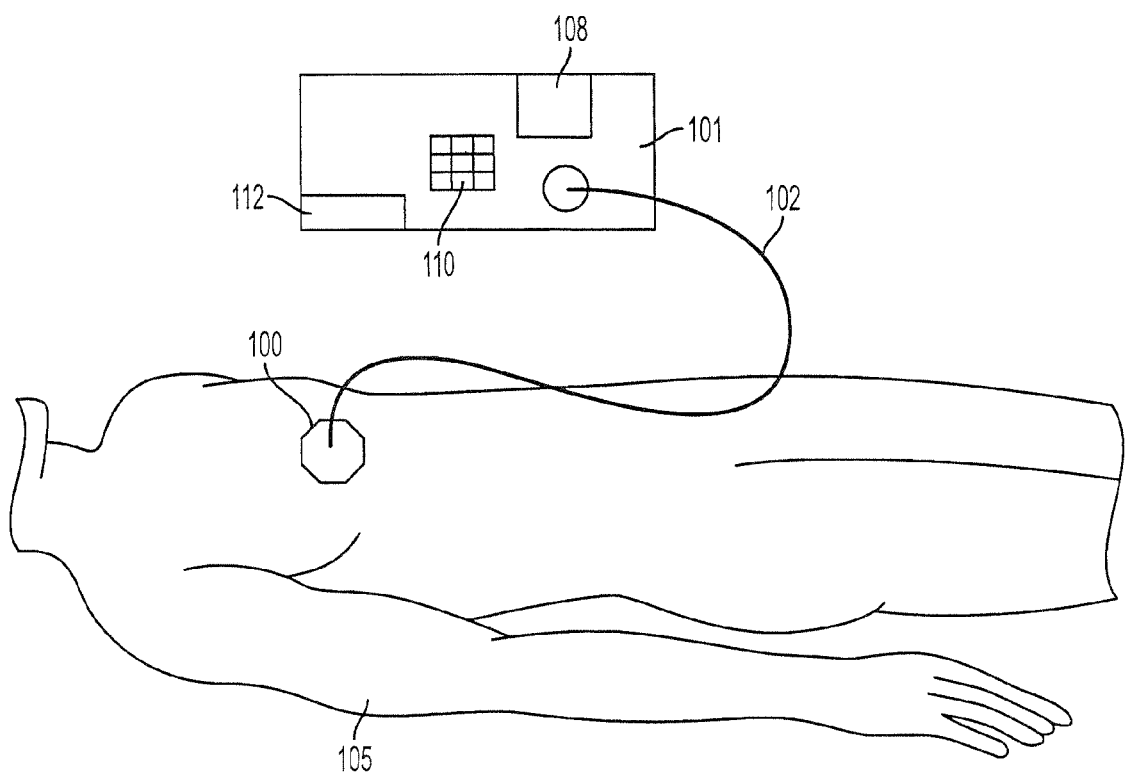
FIG. 1 shows a system for applying a pressure pulse to a skin surface in accordance with one embodiment of the invention.

FIG. 1 shows a device for treating soft body tissues, such as adipose tissue, in accordance with one embodiment of the invention. An applicator 100, to be described in detail below, is adapted to be applied to the skin of an individual 105. The applicator 100 is connected to a control unit 101 via electrical wires in a cable 102. The control unit 101 includes a power source 108. The control unit 101 also contains a temperature affecting unit 112 that cools a fluid such as ethanol or water for maintaining the applicator 100 at a predetermined temperature as explained below. The control unit 101 has an input device such as a keypad 110 that allows an operator in input selected values of parameters of the treatment, such as the intensity of the positive and negative phases, the duration of the pulses and a pulse repetition rate.

Figure 2:
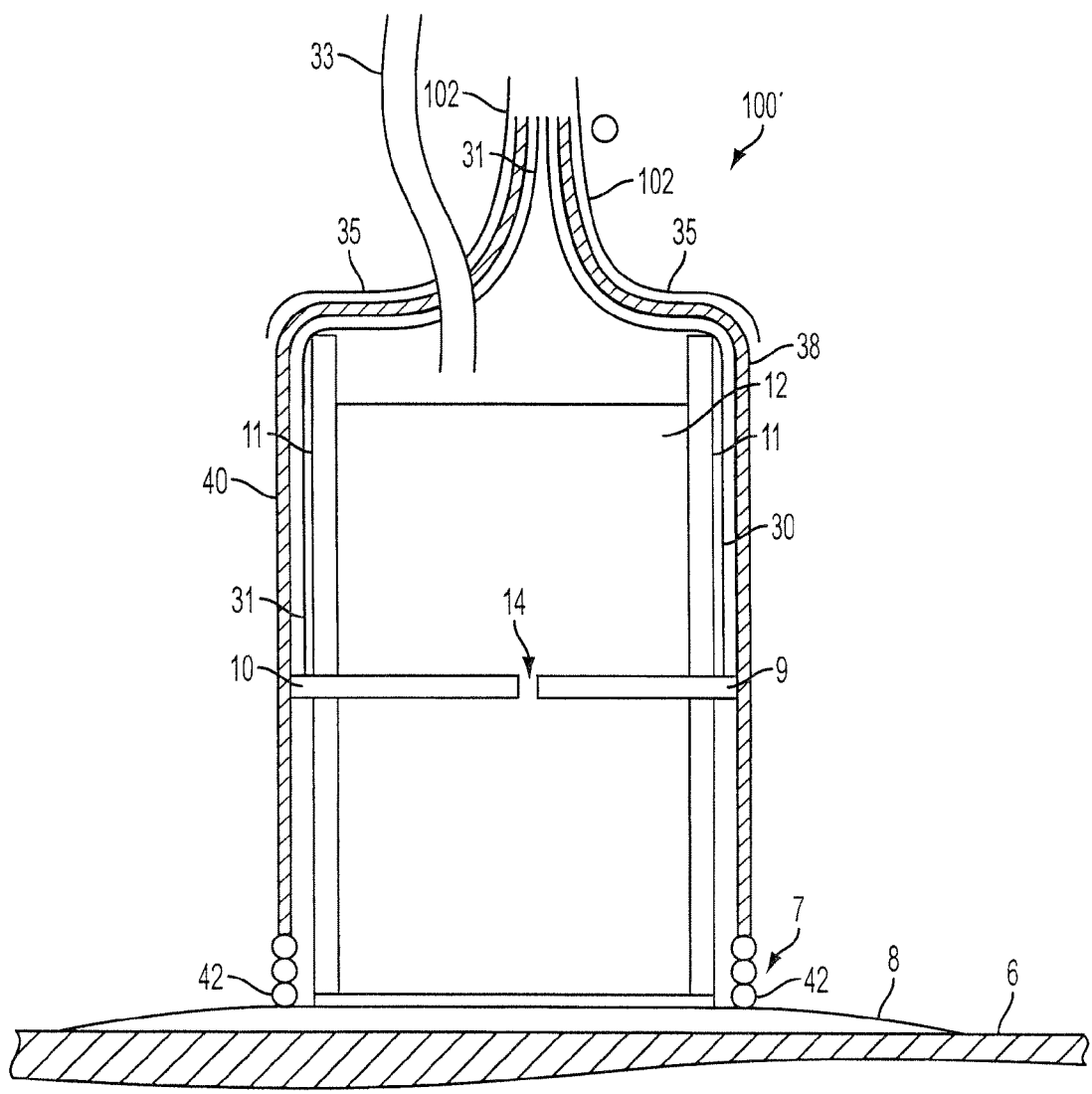
FIG. 2 shows an applicator for use in the system of FIG. 1.

FIG. 2 shows an applicator 100' that may be used for the applicator 100 shown in FIG. 1, in accordance with one embodiment of the invention. The applicator 100' creates a positive and negative pressure pulse by generating a spark in a liquid. The applicator 100' has a cylindrical vessel 11 made from an electrically insulating material such as hard rubber or plastic. The vessel 11 is closed at the application end with a flexible membrane 7. Two diametrically opposed conducting electrodes 9 and 10 extend from the wall of the vessel 11 so as to produce a small gap 14 between them. Preferably, the gap 14 is between 0.1 mm to 2 mm. The electrodes 9 and 10 are connected to the power source 108 via electrical wires 30 and 31, respectively, in the cable 102.

Before applying the applicator 100' to the skin surface 6, a thin layer of gel 8 is applied to the skin surface 6 over the adipose tissue 5 to be treated. The flexible membrane 7 of the applicator is firmly applied to a gel layer 8. The gel functions as a matching medium that couples the energy delivery from the applicator to the skin surface. The membrane 7 forms an energy delivery surface. The distance between the gap 14 and the flexible membrane 7 is at least 3 mm, preferably between 5 mm to 50 mm, more preferably between 15 to 30 mm. The vessel 11 is filled with a liquid 12, preferably water, more preferably a saline solution, and still more preferably a saline solution having a concentration between 0.1% to 2% (w/v). The vessel 11 may be open at the top to ambient atmosphere, so that the liquid 12 is at atmospheric pressure. Alternatively, the vessel may be covered at the top by a cover 35 as shown in FIG. 2. A flexible tube 33 may be inserted into the vessel 11 through the cover 35. This allows the liquid 12 to be at atmospheric pressure while preventing spilling of the liquid when the applicator 100 is applied to a skin surface in an orientation that is tilted with respect to the vertical. Alternatively, the vessel 11 may be closed and an air pump for controlling static pressure in the vessel 11 provided (not shown).

The applicator 100' is connected to the temperature affecting unit 112 in the control unit 101 via a first tube 38 and a second tube 40 in the cable 102. Cooled or heated fluid flows from the temperature affecting unit 112 to the applicator 100' via the first tube 38 in the cable 102. In the embodiment shown in FIG. 2, the fluid then flows through a coil 42 surrounding the vessel 11 and in contact with the skin surface 6 so as to cool or heat the skin surface during the treatment, as required. The fluid then flows from the applicator 100 back to the temperature affecting unit via the second tube 40 in the cable 102. In another embodiment (not shown), the fluid is a liquid that flows from the first tube 38 into the vessel 11, mixing with the liquid 12, and then leaves the vessel 11 and returns to the temperature affecting unit 112 via the second tube 40. In this embodiment, the flow of the liquid also removes any vapor bubbles in the liquid 12 generated by the spark.

The vessel may also be coupled to the treated area directly through water without a flexible membrane or gel.

The power source 108 is a pulsed power generator that is configured to deliver a high voltage pulse to the electrodes 9 and 10 so as to generate a spark in the gap 14. Typically, the pulsed power generator 108 will generate a spark having an electrical energy of about 30 Joules, at voltages between 5 to 20 kV, and a pulse duration of about 3 microseconds. Typical peak currents are about 3 kA. About 5-10% of the electrical energy in the pulsed power generator is transformed to mechanical energy in the form of pressure waves and flows in the liquid.

An applicator of the type shown in FIG. 2 was constructed having electrodes 9 and 10 made of a Copper-Tungsten alloy with a diameter of 2 mm and a gap 14 of 0.5 mm. The vessel 11 was filled with saline solution (0.9% NaCl). A pressure sensor was positioned 20 mm from the gap 14. A capacitor of 0.25 µF, charged to 15 kV, was discharged by magnetic switching to the electrodes 9 and 10, generating a spark in the gap 14 that created a vapor-filled bubble in the saline. The bubble grew to a maximum radius of about 15 mm during about 1.3 msec, and then collapsed back to a very small radius. This bubble oscillation generated a pressure pulse that was detected by the pressure sensor.

Figure 3:
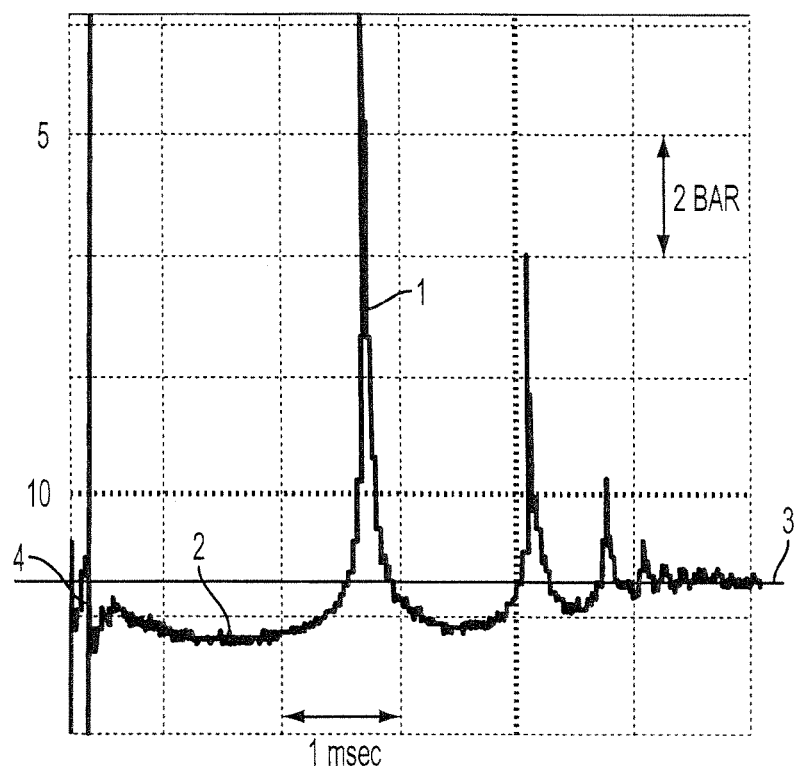
FIG. 3 shows a pressure pulse generated by the applicator of FIG. 2.

FIG. 3 shows the pressure pulse that was recorded by the pressure sensor. The horizontal time scale is 1 millisecond/div. The vertical pressure scale is 2 Bar/div where the horizontal axis 3 is the ambient atmospheric pressure. The pulse contains positive phases 1 and negative phases 2. The spark generated electromagnetic noise 4 during the first few microseconds from breakdown, which masks the primary shock.

Experiments were performed in which a sample of adipose tissue was positioned in the saline 12 approximately 20 mm from the gap 14. 30 to 300 pressure pulses of the type shown in FIG. 3 were generated in the saline. The saline was preheated to 37°. Under these conditions, the pressure pulses disrupted fat cells in the adipose tissue sample, which was revealed by the release of the fat content of the cells into the surrounding saline making the saline turbid. Disruption of the adipose cells in the adipose tissue sample was confirmed by histological examination of the tissue sample following application of the pressure wave.

Figure 4:
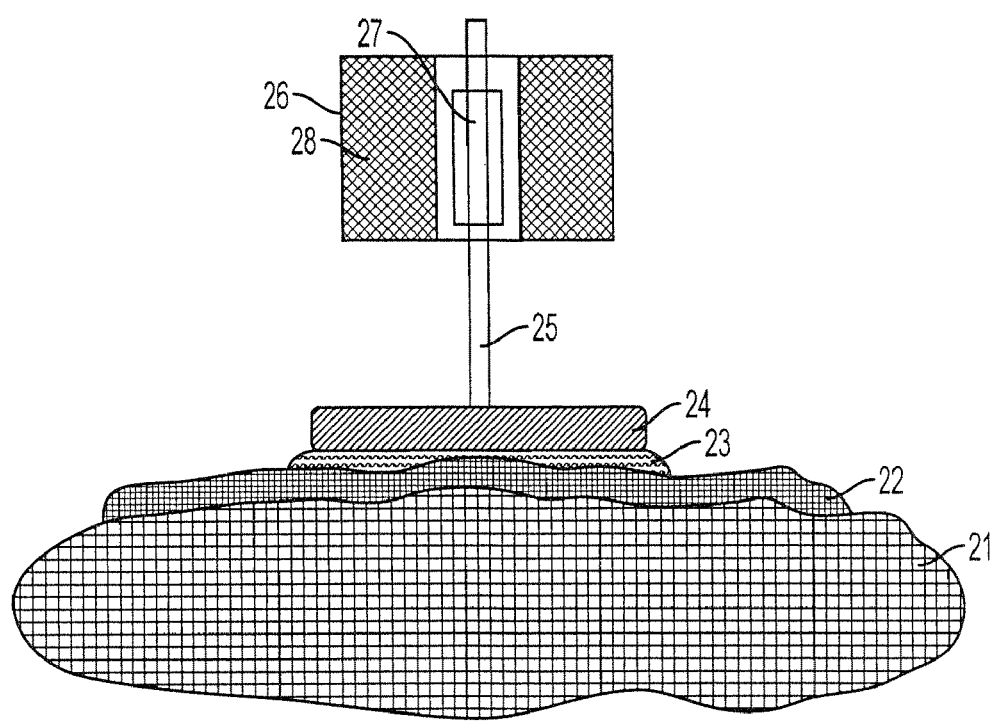
FIG. 4 shows an applicator for use in the system of FIG. 1 based on a magnetic solenoid actuator.

FIG. 4 shows an applicator 100" that may be used for the applicator 100 shown in FIG. 1. The applicator 100" includes an actuator 26 and an applicator plate 24. Applicator plate 24 can be made of a stiff or a slightly flexible solid material such as a polymeric material. The diameter of applicator plate may be, for example, between 10 to 50 mm. The applicator plate 24 is connected to the actuator 26 by a rod 25.

Before applying the applicator 100" to a skin surface 22 overlying a soft tissue layer to be treated such as adipose layer 21, a thin layer of gel 23 is applied to the skin surface. The Applicator 100" is then applied to the skin layer 22 with the applicator plate 24 in contact with the gel layer 23 so as to adhere the applicator plate to the skin surface 22. The gel layer 23 can be replaced with any slightly sticky material.

The actuator 26 is configured to exert a "push-pull" action on the rod 25, which, in turn, exerts a "push-pull" action on the applicator plate 24. The "push-pull" action has a "push" phase and a "pull" phase. In the "push" phase of the "push-pull" action, the rod 25 and actuator plate 24 are displaced by the actuator 26 towards the skin surface 22 so as to generate a positive pressure on the adipose layer 21. In the "pull" phase, the rod 25 and actuator plate 24 are displaced by the actuator 26 away the skin surface 22 so as to generate a negative pressure on the adipose layer 21. In the case of adipose tissue, the "push-pull" action has a period and amplitude selected to effect maximum destruction of fat cells and minimal damage to other tissues. Preferably, the pull phase lasts between 0.1 milliseconds to 100 milliseconds, and more preferably between 1 to 10 milliseconds. The "push" phase may be slower than the "pull" phase to generate a positive pressure on the adipose tissue 21 so as to restore the adipose tissue 21 to its original position after the "pull" phase. A strong and fast "push" phase may precede the "pull" phase, so as to generate maximum strain in the tissue prior to the "pull" phase. A train of alternating "push" phases and "pull" phases may also be used. Typically, the displacement of the applicator plate 24, and hence the skin surface 22 is between 1 to 5 mm peak to peak. Typical forces provided by the actuator 26 are from 10-1000 Newtons.

As shown in FIG. 4, the actuator 26 is a magnetic solenoid. This is by way of example only, and any type of actuator that can provide the required forces for the required time may be used. Such actuators include, for example, compressed gas actuators, motor actuators and spring actuators. The solenoid actuator 26 includes a coil 28 and a magnetic element 27. A current pulse through the coil 28 generates a magnetic force that displaces the magnetic element 27, and hence the rod 25 and actuator plate 24. When a current pulse moves in a one direction in the coil 28, the magnetic element is displaced towards the skin layer 22, so as to create a positive pressure on the skin layer 22 and underlying adipose layer 21 by the actuator plate. When a current pulse moves in the opposite direction in the coil 28, the magnetic element is displaced away from the skin layer 22, so as to create a negative pressure on the skin layer 22 and underlying adipose layer 21 by the actuator plate which is adhered to the skin surface 22 by the gel 23.

The invention claimed is:

1. A method for non-invasive treatment of a soft tissue volume, causing destruction of fat cells, with little or no damage to other cells, said method comprising:
    a) applying at least one pressure pulse to a region of skin surface overlying the soft tissue volume,
    the pressure pulse having negative pressure phases and positive pressure phases with respect to ambient pressure,
    with the positive pressure phases being slower than the negative pressure phases; and
    b) applying a temperature effector and raising the temperature of the soft tissue volume during treatment to a temperature above 37° C. by applying RF energy to the soft tissue.

2. The method according to claim 1, wherein at least one of the negative pressure phases has an intensity between 0.1 Bar and 10 Bars below ambient pressure.

3. The method according to claim 1, wherein at least one of the negative pressure phases has a duration between 0.1 millisecond and 100 milliseconds.

4. The method according to claim 1, wherein at least one of the positive pressure phases has an intensity between 1 and 30 Bars above ambient pressure.

5. The method according to claim 1, wherein at least one of the positive pressure phases has a duration between 0.01 msec to 1 msec.

6. The method according to claim 1, further comprising applying a matching medium coupling energy delivery from an applicator to the skin surface.

7. The method according to claim 6, wherein the matching medium is a liquid or gel.

8. The method according to claim 1, further comprising cooling the skin surface.

* * * * *